(12) United States Patent
Machamer et al.

(10) Patent No.: US 11,490,905 B2
(45) Date of Patent: *Nov. 8, 2022

(54) SYSTEMS AND METHODS FOR INTRAMEDULLARY NAIL IMPLANTATION

(71) Applicant: GLOBUS MEDICAL, INC., Audubon, PA (US)

(72) Inventors: David Machamer, Glen Mills, PA (US); David R. Jansen, Glenmoore, PA (US); Mark Hedgeland, Wayne, PA (US); Mark Rossney, Downingtown, PA (US)

(73) Assignee: Globus Medical, Inc., Audubon, PA (US)

( * ) Notice: Subject to any disclaimer, the term of this patent is extended or adjusted under 35 U.S.C. 154(b) by 448 days.

This patent is subject to a terminal disclaimer.

(21) Appl. No.: 16/670,472

(22) Filed: Oct. 31, 2019

(65) Prior Publication Data
US 2020/0069318 A1 Mar. 5, 2020

Related U.S. Application Data

(63) Continuation of application No. 15/862,687, filed on Jan. 5, 2018, now Pat. No. 10,492,803, which is a continuation-in-part of application No. 15/441,457, filed on Feb. 24, 2017, now Pat. No. 10,307,197, which is a continuation-in-part of application No.
(Continued)

(51) Int. Cl.
*A61B 17/17* (2006.01)
*A61B 17/16* (2006.01)
*A61B 17/72* (2006.01)

(52) U.S. Cl.
CPC ...... *A61B 17/1717* (2013.01); *A61B 17/1615* (2013.01); *A61B 17/1725* (2013.01); *A61B 17/72* (2013.01); *A61B 17/7233* (2013.01)

(58) Field of Classification Search
USPC ...... 600/201, 204, 206, 226; 606/62, 64, 96, 606/98
See application file for complete search history.

(56) References Cited

U.S. PATENT DOCUMENTS

| 4,103,683 A | 8/1978 | Neufeld |
| 4,541,424 A | 9/1985 | Grosse et al. |

(Continued)

FOREIGN PATENT DOCUMENTS

| CA | 2373716 A1 | 11/2001 |
| CN | 201578353 U | 9/2010 |

(Continued)

*Primary Examiner* — Eduardo C Robert
*Assistant Examiner* — David C Comstock

(57) ABSTRACT

Intramedullary nails, systems, and methods. The intramedullary nail may include a generally elongate body extending from a first, distal end to a second, proximal end. The distal end may include one or more openings configured to receive one or more bone anchors that extend transversely through the distal end of the intramedullary nail, and thereby configured to secure the distal end of the nail. The proximal end may also include one or more openings configured to receive one or more bone anchors that extend transversely through the proximal end of the intramedullary nail, and thereby configured to secure the proximal end of the nail.

10 Claims, 11 Drawing Sheets

Related U.S. Application Data

15/423,773, filed on Feb. 3, 2017, now Pat. No. 10,251,691, which is a continuation-in-part of application No. 15/272,850, filed on Sep. 22, 2016, now Pat. No. 10,299,847.

(60) Provisional application No. 62/569,763, filed on Oct. 9, 2017.

(56) References Cited

U.S. PATENT DOCUMENTS

| | | | |
|---|---|---|---|
| 4,545,374 A * | 10/1985 | Jacobson | A61B 17/32056 604/164.11 |
| 4,667,664 A | 5/1987 | Taylor et al. | |
| 4,878,915 A | 11/1989 | Brantigan | |
| 4,920,958 A * | 5/1990 | Walt | A61B 17/1714 606/103 |
| 4,952,213 A | 8/1990 | Bowman et al. | |
| 4,978,349 A | 12/1990 | Frigg | |
| 5,041,115 A | 8/1991 | Frigg et al. | |
| 5,167,666 A | 12/1992 | Mattheck et al. | |
| 5,234,434 A | 8/1993 | Goble et al. | |
| 5,267,958 A | 12/1993 | Buchbinder et al. | |
| 5,354,300 A * | 10/1994 | Goble | A61F 2/0811 606/104 |
| 5,433,720 A | 7/1995 | Facciolo et al. | |
| 5,499,986 A | 3/1996 | Dimarco | |
| 5,549,610 A | 8/1996 | Russell et al. | |
| 5,613,971 A | 3/1997 | Lower et al. | |
| 5,674,225 A | 10/1997 | Muller | |
| 5,728,128 A | 3/1998 | Crickenberger et al. | |
| 5,741,256 A | 4/1998 | Bresina | |
| 5,743,908 A | 4/1998 | Kim | |
| 5,899,906 A | 5/1999 | Schenk | |
| 6,010,506 A | 1/2000 | Gosney et al. | |
| 6,016,727 A | 1/2000 | Morgan | |
| 6,039,739 A * | 3/2000 | Simon | A61B 17/1725 606/62 |
| 6,106,528 A | 8/2000 | Durham et al. | |
| 6,120,504 A | 9/2000 | Brumback et al. | |
| 6,210,414 B1 | 4/2001 | Lin | |
| 6,235,031 B1 | 5/2001 | Hodgeman et al. | |
| 6,319,253 B1 | 11/2001 | Ackeret et al. | |
| 6,187,007 B1 | 12/2001 | Frigg et al. | |
| 6,406,477 B1 | 6/2002 | Fujiwara | |
| 6,409,730 B1 | 6/2002 | Green et al. | |
| 6,436,100 B1 | 8/2002 | Berger | |
| 6,461,360 B1 | 10/2002 | Adam | |
| 6,547,791 B1 | 4/2003 | Buhren et al. | |
| 6,565,573 B1 | 5/2003 | Ferrante et al. | |
| 6,702,816 B2 | 3/2004 | Buhler | |
| 6,835,197 B2 | 12/2004 | Roth et al. | |
| 6,908,465 B2 | 6/2005 | von Hoffmann et al. | |
| 6,926,707 B2 | 8/2005 | Nash et al. | |
| 7,217,246 B1 | 5/2007 | Stone | |
| 7,247,156 B2 | 7/2007 | Ekholm et al. | |
| 7,311,710 B2 | 12/2007 | Zander | |
| 7,410,488 B2 | 8/2008 | Janna et al. | |
| 7,476,225 B2 | 1/2009 | Cole | |
| 7,549,994 B2 | 6/2009 | Zander et al. | |
| 7,621,913 B2 | 11/2009 | Semet | |
| 7,686,808 B2 | 3/2010 | Orbay et al. | |
| 7,722,611 B2 | 5/2010 | Cavallazzi et al. | |
| 7,763,022 B2 | 7/2010 | Speitling et al. | |
| 7,780,667 B2 | 8/2010 | Wantanabe et al. | |
| 7,799,030 B2 | 9/2010 | Wantanabe et al. | |
| 7,837,709 B2 | 11/2010 | Dutoit et al. | |
| 7,914,532 B2 | 3/2011 | Shaver et al. | |
| 7,927,336 B2 | 4/2011 | Rasmussen | |
| D638,125 S | 5/2011 | Velikov | |
| D638,126 S | 5/2011 | Velikov | |
| 8,057,476 B2 | 11/2011 | Ekholm et al. | |
| 8,083,742 B2 | 12/2011 | Martin | |
| 8,092,454 B2 | 1/2012 | Sohngen | |
| 8,100,911 B2 | 1/2012 | Yamazaki et al. | |
| 8,114,079 B2 | 2/2012 | Haidukewych et al. | |
| 8,137,348 B2 | 3/2012 | Gotfried | |
| 8,172,841 B2 | 5/2012 | Defossez | |
| 8,187,281 B2 | 5/2012 | Cresina et al. | |
| 8,187,309 B2 | 5/2012 | Castaneda et al. | |
| 8,241,286 B2 | 8/2012 | Metzinger et al. | |
| 8,262,658 B2 | 9/2012 | Schlienger et al. | |
| 8,277,450 B2 | 10/2012 | Dees, Jr. et al. | |
| 8,303,590 B2 | 11/2012 | Elghazaly et al. | |
| 8,317,788 B2 | 11/2012 | Kaup | |
| 8,317,789 B2 | 11/2012 | LeCronier et al. | |
| 8,328,805 B2 | 12/2012 | Cole | |
| 8,360,970 B2 | 1/2013 | Mangiardi | |
| 8,414,584 B2 | 4/2013 | Brigido | |
| 8,449,544 B2 | 5/2013 | Grusin | |
| 8,454,606 B2 | 6/2013 | Frigg et al. | |
| 8,491,584 B1 | 7/2013 | Fagan | |
| 8,518,040 B2 | 8/2013 | Schlienger et al. | |
| RE44,501 E | 9/2013 | Janna et al. | |
| 8,562,606 B2 | 10/2013 | Richter et al. | |
| 8,585,744 B2 | 11/2013 | Duggal et al. | |
| 8,591,513 B2 | 11/2013 | Overes et al. | |
| 8,668,695 B2 | 3/2014 | Schwammberger et al. | |
| 8,715,283 B2 | 5/2014 | Brumfield et al. | |
| 8,740,902 B2 | 6/2014 | Brodsky et al. | |
| 8,764,752 B2 | 7/2014 | Buettler et al. | |
| 8,790,343 B2 | 7/2014 | McClellan et al. | |
| 8,808,292 B2 | 8/2014 | Velikov | |
| 8,808,293 B2 | 8/2014 | Buettler et al. | |
| 8,834,469 B2 | 9/2014 | Wantanabe et al. | |
| 8,906,023 B2 | 12/2014 | Matityahu et al. | |
| 8,932,301 B2 | 1/2015 | Metzinger et al. | |
| 8,945,136 B2 | 2/2015 | Overes et al. | |
| 8,961,518 B2 | 2/2015 | Taylor et al. | |
| 8,992,587 B2 | 3/2015 | Kirschman | |
| 9,072,552 B2 | 7/2015 | Simon et al. | |
| 9,101,432 B2 | 8/2015 | Limouze et al. | |
| 9,119,645 B2 | 9/2015 | McBride | |
| 9,138,278 B2 | 9/2015 | Van Osten, III | |
| 9,155,582 B2 | 10/2015 | Felder et al. | |
| 9,295,504 B2 | 3/2016 | Haidukewych et al. | |
| 9,358,049 B2 | 6/2016 | Simon et al. | |
| RE46,078 E | 7/2016 | Janna et al. | |
| 9,387,019 B2 | 7/2016 | Duggal et al. | |
| 9,393,064 B2 | 7/2016 | Roethlisberger et al. | |
| 9,408,645 B2 | 8/2016 | Graca et al. | |
| 9,421,049 B2 | 8/2016 | Rogachefsky | |
| 9,427,266 B2 | 8/2016 | Kmiec, Jr. | |
| 9,433,448 B2 | 9/2016 | Ehmke et al. | |
| 9,474,557 B2 | 10/2016 | Schwammberger et al. | |
| 9,241,744 B2 | 11/2016 | Blake et al. | |
| 9,532,818 B2 | 1/2017 | Schwammberger et al. | |
| 9,597,129 B2 | 3/2017 | Keller et al. | |
| 9,675,363 B2 | 6/2017 | Abbasi | |
| 9,724,108 B2 | 8/2017 | Prien | |
| 2003/0018340 A1 | 1/2003 | Branch | |
| 2006/0111716 A1 | 5/2006 | Schlienger et al. | |
| 2006/0200160 A1 | 9/2006 | Border et al. | |
| 2007/0118119 A1 | 5/2007 | Hestad | |
| 2007/0123878 A1 | 5/2007 | Shaver et al. | |
| 2008/0154264 A1 | 6/2008 | Wack et al. | |
| 2009/0088604 A1 | 4/2009 | Lowry et al. | |
| 2010/0234846 A1 | 9/2010 | Eglseder | |
| 2010/0274254 A1 | 10/2010 | Boileau et al. | |
| 2011/0196372 A1 | 8/2011 | Murase | |
| 2011/0245885 A1 | 10/2011 | Powell | |
| 2011/0282347 A1 | 11/2011 | Gordon et al. | |
| 2013/0190570 A1 | 6/2013 | Hirsch et al. | |
| 2013/0282016 A1 | 10/2013 | Volpi et al. | |
| 2013/0289572 A1 | 10/2013 | Broome | |
| 2013/0317502 A1 | 11/2013 | Overes et al. | |
| 2013/0325076 A1 | 12/2013 | Palmer et al. | |
| 2014/0081281 A1* | 3/2014 | Felder | A61B 17/17 606/96 |
| 2014/0243838 A1 | 8/2014 | Feibel et al. | |
| 2014/0276828 A1 | 9/2014 | Howling et al. | |
| 2014/0309648 A1 | 10/2014 | Matityahu | |
| 2015/0038967 A1 | 2/2015 | Khong et al. | |
| 2015/0150567 A1 | 6/2015 | Okuno et al. | |

(56) References Cited

U.S. PATENT DOCUMENTS

| | | |
|---|---|---|
| 2015/0265323 A1 | 9/2015 | Sems et al. |
| 2016/0030064 A1 | 2/2016 | Dacosta et al. |
| 2016/0051295 A1 | 2/2016 | Nakamura et al. |
| 2016/0089159 A1* | 3/2016 | Ardito ................ A61B 17/1764 606/96 |
| 2016/0089189 A1 | 3/2016 | Buscaglia et al. |
| 2016/0256202 A1 | 9/2016 | Halder |
| 2016/0262819 A1 | 9/2016 | May et al. |
| 2017/0202566 A1 | 7/2017 | Luo et al. |
| 2020/0113712 A1* | 4/2020 | Luna ..................... A61F 2/4606 |

FOREIGN PATENT DOCUMENTS

| | | |
|---|---|---|
| CN | 203263518 U | 11/2013 |
| DE | 3722852 A1 | 1/1989 |
| DE | 4240277 A1 | 6/1993 |
| DE | 102008020193 A1 | 10/2009 |
| DE | 102014109935 A1 | 10/2009 |
| DE | 102009010328 A1 | 8/2010 |
| EP | 257118 | 3/1988 |
| EP | 2548523 A1 | 1/2013 |
| EP | 3466357 A1 | 4/2019 |
| FR | 2965471 | 4/2012 |
| JP | 2973316 B1 | 11/1999 |
| JP | 2000342596 | 12/2000 |
| WO | 2009002890 A1 | 12/2008 |
| WO | 201203354 A1 | 8/2012 |
| WO | 2012103335 A1 | 8/2012 |
| WO | 2016059347 A1 | 4/2016 |
| WO | 2016082861 A1 | 6/2016 |

* cited by examiner

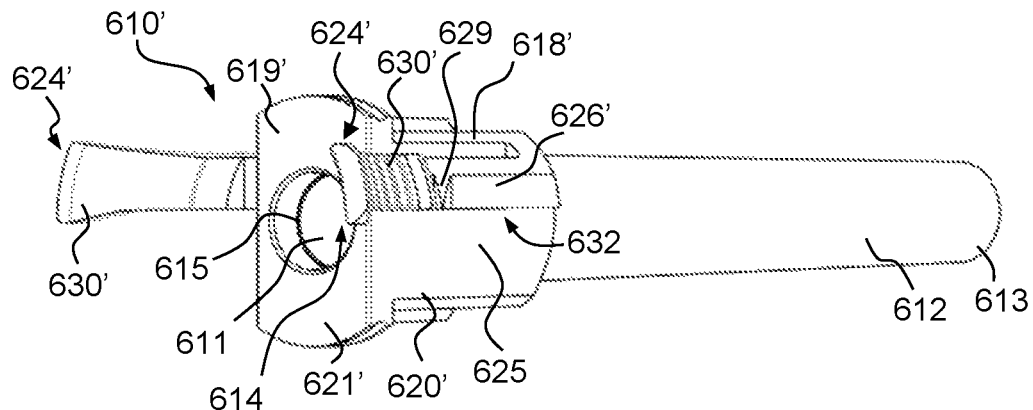
FIG. 25
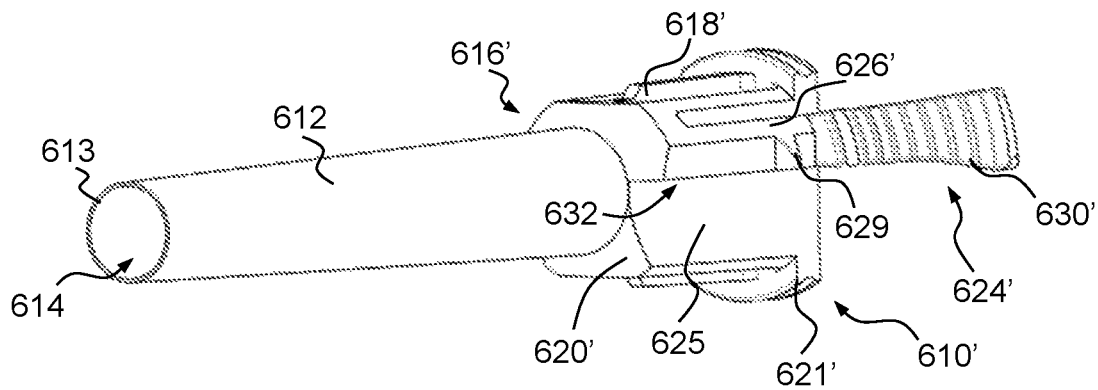
FIG. 26
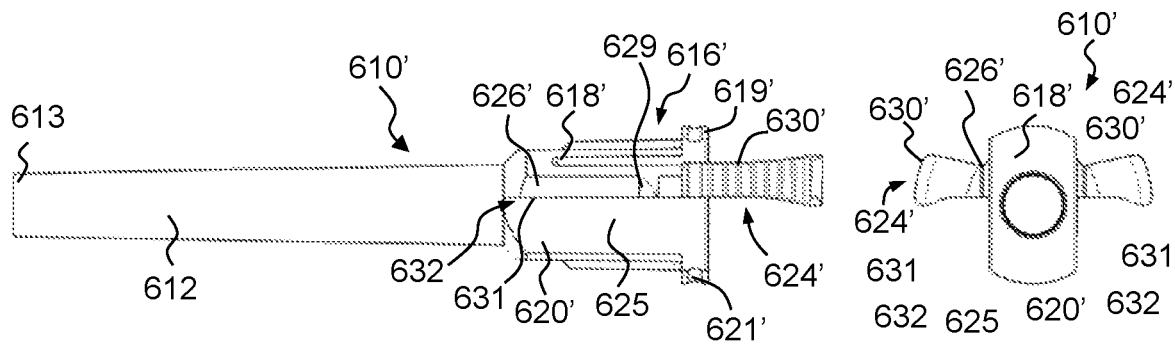
FIG. 27
FIG. 28

SYSTEMS AND METHODS FOR INTRAMEDULLARY NAIL IMPLANTATION

CROSS REFERENCE TO RELATED APPLICATION

This application is a continuation of U.S. application Ser. No. 15/862,687, filed Jan. 5, 2018, which is a continuation-in-part of U.S. application Ser. No. 15/441,457, filed Feb. 24, 2017, which is continuation-in-part of U.S. application Ser. No. 15/423,773, filed on Feb. 3, 2017, which is a continuation-in-part of U.S. application Ser. No. 15/272,850, filed on Sep. 22, 2016. This application also claims the benefit of U.S. Provisional Application Ser. No. 62/569,763, filed on Oct. 9, 2017. The contents of each of these applications are incorporated herein by reference in their entirety for all purposes.

TECHNICAL FIELD

The present technology is generally related to intramedullary nail implantation for treatment of bone fractures. In particular, several embodiments are directed to systems and methods for implanting an intramedullary nail for immobilizing bone fractures.

BACKGROUND

The significant long bones of the extremities are the humerus, radius and ulna of the upper extremity and the femur and tibia of the lower extremity. Following an injury to the long bone, and in particular, injuries resulting in one or more fractures of the long bone, one or more fixation devices may be used to immobilize the fracture fragments and stabilize the long bone. Bone fractures can be treated with screws or other fixation devices inserted into or through the bone to stabilize it once the fractured portions have been brought into proper alignment. Femoral neck fixation, for example, can be used to treat hip fractures by inserting an intramedullary nail into the medullary cavity of the fractured femur followed by insertion of a fixation screw into the femoral neck/head at an angle relative to the intramedullary nail. Similarly, other long bone fractures can be treated by inserting an intramedullary nail into the intramedullary canal of the bone and providing the appropriate proximal and/or distal fixation. Traditional intramedullary devices may suffer from a number of disadvantages, however. For example, they may be susceptible to implant failure and difficulty in alignment of the fixation screw with respect to the intramedullary nail. Accordingly, there is a need for improved systems and methods for intramedullary nail implantation.

SUMMARY

Intramedullary nails, systems, insertion tools, and method of treatment are provided. The intramedullary nails may be suitable for implanting within a medullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although generally described with reference to the femur and tibia, it will be appreciated that the intramedullary nail and system may be adapted for use with any long bone.

According to one aspect, an intramedullary nail is provided. The intramedullary nail may comprise a generally elongate body extending from a first, distal end to a second, proximal end. The distal end may include one or more openings configured to receive one or more bone anchors or fasteners that extend transversely through the distal end intramedullary nail, and thereby configured to secure the distal end of the nail. The proximal end may also include one or more openings configured to receive one or more bone anchors or fasteners that extend transversely through the proximal end of the intramedullary nail, and thereby configured to secure the proximal end of the nail.

In accordance with another aspect, a system for inserting an intramedullary nail into a bone is provided. The system includes an intramedullary nail having a proximal end, a distal end, at least one side surface extending between the proximal end and the distal end, and an aperture through the intramedullary nail. An insertion tool includes a handle portion, a coupling portion and an aiming guide. The handle portion defines a first connection assembly. The coupling portion extends from the handle portion and is configured to removably couple to the proximal end of the intramedullary nail. The aiming guide has a body with at least one support block and a second connection assembly. The first and second connection assemblies are configured to releasably interconnect the handle portion and the aiming guide. The at least one guide block defines a guide sheath hole configured to receive a guide sheath therethrough. The guide sheath hole is positioned such that, when the intramedullary nail is coupled to the coupling portion, the guide sheath hole substantially aligns with the aperture in the intramedullary nail.

In accordance with another aspect, an intramedullary nail system is provided. The system includes an intramedullary nail having a body extending between a proximal end and a distal end with a substantial portion of the body elongated along a first axis. The body has a proximal portion and a distal portion. A first opening is formed through the proximal portion of the body and a second opening is formed through the distal portion of the body. At least the first and second openings are formed with a two-start thread.

In accordance with another aspect, a system for inserting an intramedullary nail into a bone is provided. The system includes an intramedullary nail having a body which defines a proximal portion and a distal portion, with at least first and second openings defined through the proximal portion of the body. An insertion tool includes an aiming guide having an arcuate body defining at least two hole openings therethrough. Each of the hole openings is axially aligned with a respective one of the first and second openings and configured to receive a guide sheath therethrough. A friction retention assembly is associated with each hole opening and includes a friction pad which retractably extends into the hole opening to engage a guide sheath positioned therein.

In accordance with another aspect, a cannula system for inserting an intramedullary nail into a bone is described. The cannula system system includes a cannula assembly and a drill sleeve. The cannula assembly includes a flexible cannula extending from a rigid handle with a through passage extending through the flexible cannula and the rigid handle. The flexible cannula and the rigid handle further define axial pin slots extending adjacent to the through passage. The drill sleeve includes a sleeve portion configured to be received in the flexible cannula. A housing portion from which the sleeve portion extends is configured such that a portion thereof is received in the through passage within the rigid handle. A pair of release triggers are hingedly connected to the housing portion. Each release trigger defines at least one projection configured to releasably engage within the rigid handle to lock the drill sleeve relative to the cannula assembly. Each of the release triggers further defines a guide area which aligns with a respective axial pin slot such that a fixation pin may be passed past the housing portion and through the axial pin slot.

Also provided are kits including intramedullary nails of varying shapes and sizes, bone anchors, fasteners, insertion tools, and components for installing the same.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIGS. 13-30 illustrate various views of illustrative cannula systems and illustrative drill sleeves.

DETAILED DESCRIPTION

Figure 1:
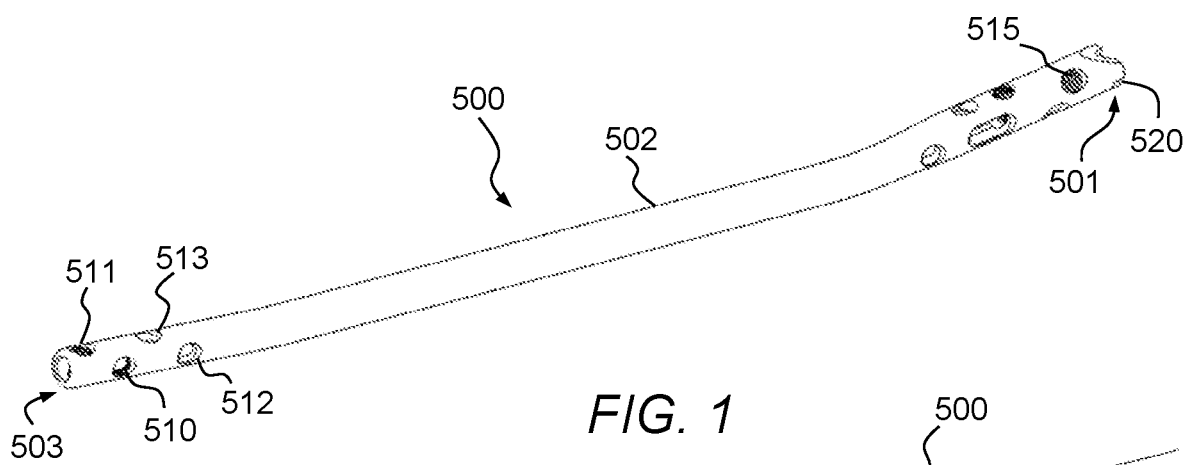
FIGS. 1-4 illustrate various views of illustrative tibial nails.
Figure 2:
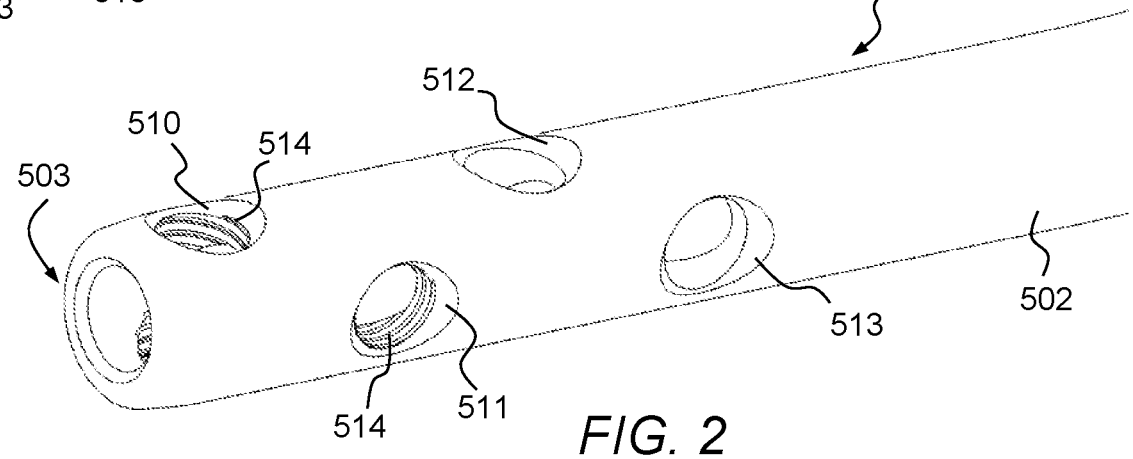
Figure 3:
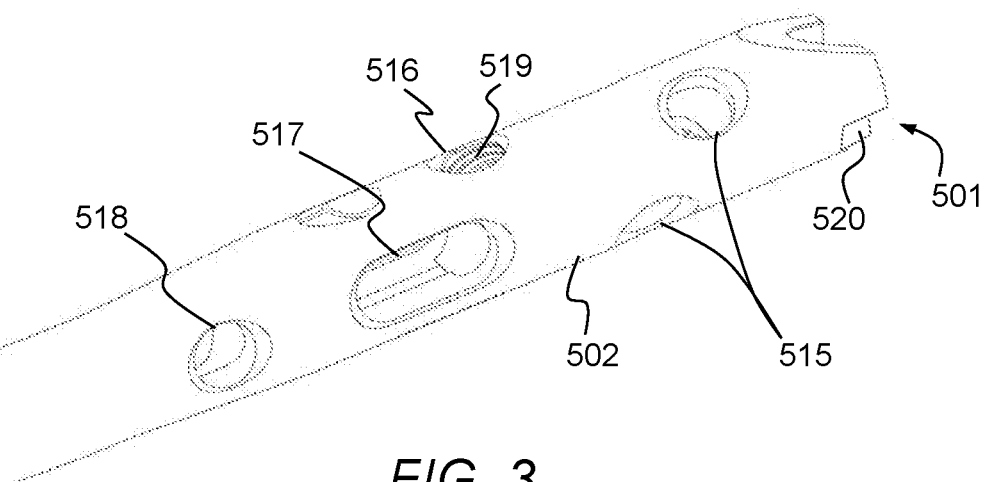
Figure 4:
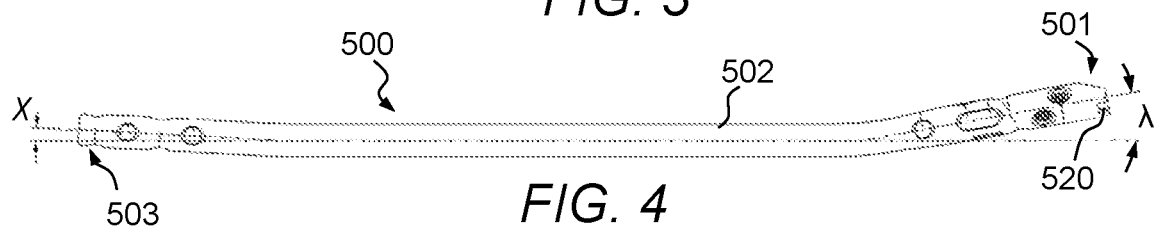

Intramedullary nails, systems, insertion tools, and method of treatment are provided. The intramedullary nails may be suitable for implantation within the intramedullary canal of a fractured long bone and subsequently providing proximal fixation and/or distal fixation, for example, with one or more anchors, fasteners, fixation screws, or the like. Suitable long bones may include the humerus, radius, ulna, femur, tibia, or the like. Although further described with reference to hip fractures of the femur or fractures of the tibia, it will be appreciated that the intramedullary nail and system may be adapted for use with any long bone.

In conventional hip fracture fixation techniques, there are four main failure modes: axial cutout, cephalad cutout, proximal fragment rotation, and nonunion. "Cutout" is the term for hip screw subsidence into the articular surface of the hip. Cutout can occur in either a cephalad (toward the head) or axial direction (along the axis of the hip screw). Axial cutout is the result of an implant with a small axial profile that provides little resistance to axial translation. Axial cutout can be addressed by the "controlled collapse" features on certain modern hip fracture nails; the hip screw is allowed to translate through the nail, even after the set screw is locked in place. Cephalad cutout is the radial translation of the nail which is the result of a narrow implant that "windshield wipers" through the weak cancellous bone in the hip. Proximal fragment rotation is the result of a circular profile hip screw that acts as a fulcrum to the proximal hip fragment. Fracture nonunion is the result of biologic or mechanical factors that are incompatible with the bone healing process. Biologic factors of the patient are not controllable by the implant. Mechanical factors are those that typically allow fixation that is too rigid or too flexible. Nonunion is usually the precursor to one of the other three failure modes. Occasionally, nonunion will cause the nail to break in fatigue before the bone fails.

The intramedullary nails and systems described herein may address one or more of these failure modes. In some embodiments, the intramedullary nail includes proximal and distal locking, for example, to prevent cutout. In other embodiments, the intramedullary nail may include proximal locking including two interlocking fixation devices (e.g., screws), for example, by providing converging and diverging purchase, along with bony fixation in the calcar of the femur, which is the strongest portion of the hip bone. Accordingly, the risk of failure due to cutout and/or rotation can be reduced.

Additionally, some intramedullary nail implantation systems fail to adequately address the problems of fragment rotation during implantation. Rotation occurs when fragments of the bone rotate about the axis of the screw during the implantation procedure. Conventional anti-rotation technologies require the use of additional instruments or are limited to a single wire placement. In some embodiments, an insertion tool is directly coupled to the intramedullary nail and additional instruments are not needed for the placement of an anti-rotation guide wire and allow the user to place one or more guide wires anterior and/or posterior to the nail. These guide wires can be positioned to prevent the distal fragments of the femoral head and neck from rotating about the axis of the anchor during the procedure.

Some systems may be susceptible to backout during the implantation procedure. Backout occurs when the guide sheath used to insert the screw through the intramedullary nail moves proximally away from the bone. Conventional systems either have no features to prevent backout or else provide backout prevention measures that obstruct the normal positioning of the hands during the procedure, resulting in the risk of releasing the guide sheaths and dropping them to the floor. Ratchets on the insertion tool may have the release button facing towards the grip portion on the insertion tool and may present the danger of the user's hand slipping and inadvertently pressing the button. Accidentally pressing the button could result in releasing the sheath and causing the sheath to fall on the floor. In some embodiments, a backout prevention system (e.g., a friction system) may be disposed within the insertion tool, which allows a user to have a hand placed on the grip of the insertion tool without the risk of inadvertently pressing the ratchet release button.

Although many of the embodiments are described below with respect to devices, systems, and methods for implantation of intramedullary nails, other embodiments are within the scope of the present technology. Additionally, other embodiments of the present technology can have different configurations, components, and/or procedures than those described herein. For example, other embodiments can include additional elements and features beyond those described herein, or other embodiments may not include several of the elements and features shown and described herein.

For ease of reference, throughout this disclosure identical reference numbers are used to identify similar or analogous components or features, but the use of the same reference number does not imply that the parts should be construed to be identical. Indeed, in many examples described herein, the identically numbered parts are distinct in structure and/or function.

Referring to FIGS. 1-4, an illustrative tibial intramedullary nail 500 will be described. It is recognized that the features of the nail 500 are not limited to use in a tibial nail and may be incorporated into other intramedullary nails. The intramedullary nail 500 generally comprises an elongate body 502 extending from a first, distal portion or end 503 to a second, proximal portion or end 501. The elongate body 502 may be in the form of an elongate tubular rod configured to extend longitudinally within the intramedullary canal of a fractured bone. The elongate rod may be hollow or may be solid along its length. The elongate body may be substantially straight along a longitudinal axis of the nail 500 or may comprise one or more curves or bends to conform to the anatomical shape of the intramedullary canal. In the embodiment of the nail 500 illustrated in FIGS. 1-4, the nail 500 is utilized in a tibia and the proximal end has a bend λ relative to the shaft while the distal end has a bend χ relative to the shaft. In the illustrated embodiment, the bend λ is approximately 10° while the distal end bend χ is approximately 3°. The bends λ and χ are not limited to the described angles and may have larger or smaller bends depending on the anatomy of the bone.

The intramedullary nail 500 may be comprised of any suitable biocompatible materials. The intramedullary nail 500 may be comprised of titanium, cobalt chrome, cobalt-chrome-molybdenum, stainless steel, tungsten carbide, carbon composite, plastic or polymer—such as polyetheretherketone (PEEK), polyethylene, ultra-high molecular weight polyethylene (UHMWPE), resorbable polylactic acid (PLA), polyglycolic acid (PGA), combinations or alloys of such materials, or other appropriate biocompatible materials that have sufficient strength to secure and hold bone, while also having sufficient biocompatibility to be implanted into a body.

The distal end 503 of the tibial nail 500 contains four openings 510-513. The openings 510, 512 are oriented in the AP direction and the openings 511, 513 are oriented in the ML direction. In the illustrated embodiment, the AP opening 510 and the ML opening 511 each include a two-start thread 514 used to create a fixed angle construct with the locking screw. Fixed angle constructs are used to treat highly unstable fractures. In unstable fractures or in patients with poor bone quality, it is imperative that the surgeon has an ability to stabilize the lateral translation of the nail relative to the screw. This is often referred to as an interference fit. To achieve interference fit with a locking screw, the threaded holes 510, 511 includes threads 514 with a two-start thread. In the illustrated embodiment, the threads 514 provide a two start 60-degree machine thread. The threads 514 will have the same pitch as the threads of the screw and the screw shaft preferably also has a two-start thread for easy advancement. The threaded two-start holes 510, 511 in the nail 500 itself is an advantage over current interference holes because it is easy to manufacture, and requires no additional steps or special techniques on the part of the surgeon. In the illustrated embodiment, the most distal opening 510 is located 5 mm from the distal end of the nail 500, the next opening 511 is located 15 mm from the distal end, the next opening 512 is located 25 mm from the distal end, and the opening 513 is located 35 mm from the distal end. The opening locations are not limited to the described distances and may be positioned at different locations depending on the anatomy of the bone.

Returning to FIGS. 1 and 3, the proximal end 501 of the tibial nail 500 contains openings 515-518, including a pair of proximal oblique openings 515, an AP oblique opening 516, a proximal ML slot 517 and a proximal ML opening 518. Each of the proximal oblique openings 515 is configured to receive and guide reconstruction screws and is at an angle relative to the axis of the nail 500. The angle of each opening 515 relative to the axis is in the range of 45°-60°, and in the illustrated embodiment, are each 55°. The AP oblique opening 516 contains a two-start thread 519 used to create a fixed angle construct with a locking screw. The ML locking slot 517 facilitates relative movement between the nail 500 and the locking screw in the event compression or the like is applied during installation and also provides for static/dynamic locking modes. In the illustrated embodiment, the slot 517 is 7 mm long and starts 36 mm from the proximal end of the nail 500. The proximal oblique openings 515 are located at 14 and 20 mm from the proximal end and the ML opening is located 57 mm from the proximal end. The opening locations are not limited to the described distances and may be positioned at different locations depending on the anatomy of the bone.

In the illustrated embodiment, the proximal end 501 of the tibial nail 500 also includes a pair of connection slots 520. The connection slots 520 are configured to engage projections 549 on the insertion tool 540 to releasably connect the nail 500 to the tool 540, as will be described in more detail hereinafter. While connection slots 520 are illustrated, other coupling mechanisms, for example, internal threads within the proximal end 501 of the nail 500, may be employed.

Figure 5:
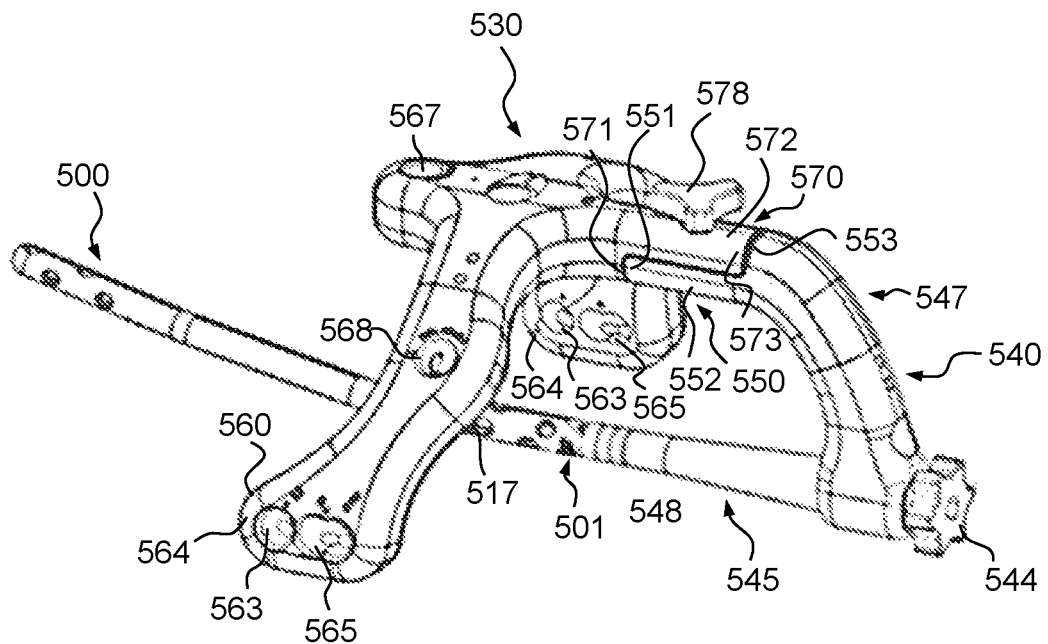
FIGS. 5-12 illustrate various views of illustrative insertion systems.

Having described various features of an illustrative tibia nail 500, tools, systems and methods of inserting the tibia nail 500 will be described with reference to FIGS. 5-30. The tibial nail 500 is inserted into the medullary canal through an incision at the entry site. FIG. 5 illustrates an illustrative embodiment of a system 530 for implanting an intramedullary nail 500 utilizing the infra-patellar approach. The infra-patellar approach is one standard approach for insertion of the tibial nail 500. This approach is typically performed with the leg in the hyper-flexed (HF) position. The tibial nail 500 is inserted directly through the incision into the tibial canal.

Figure 6:
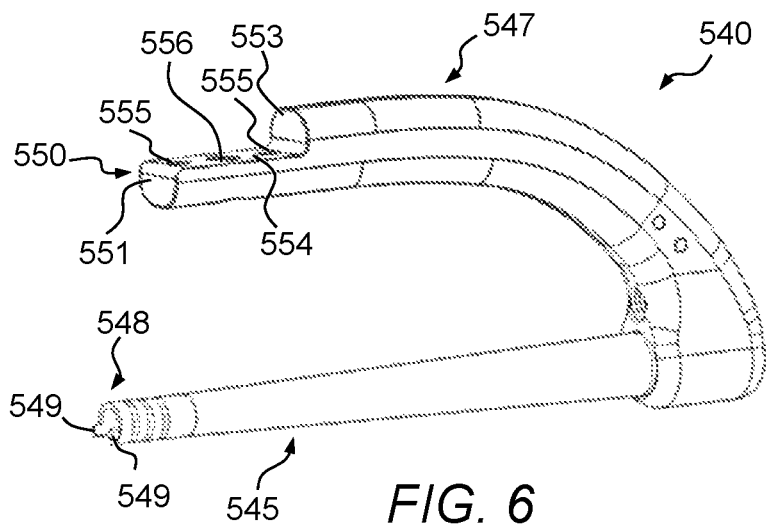
Figure 7:
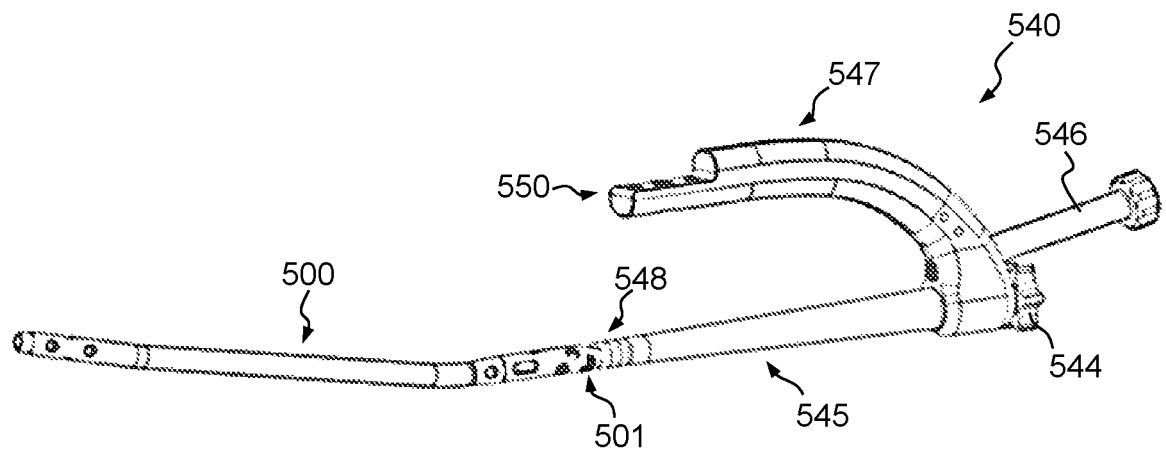
Figure 8:
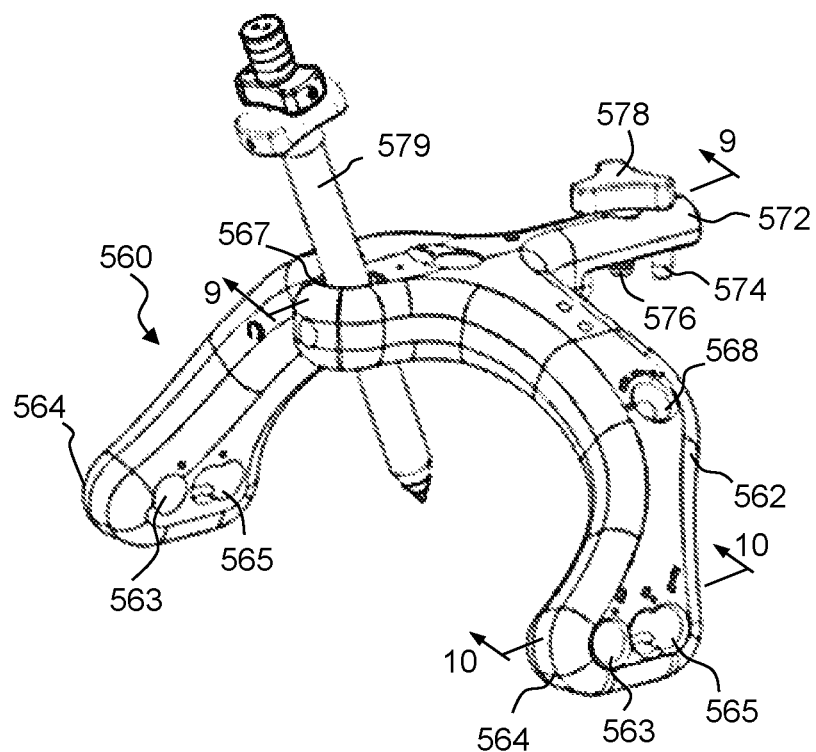
Figure 9:
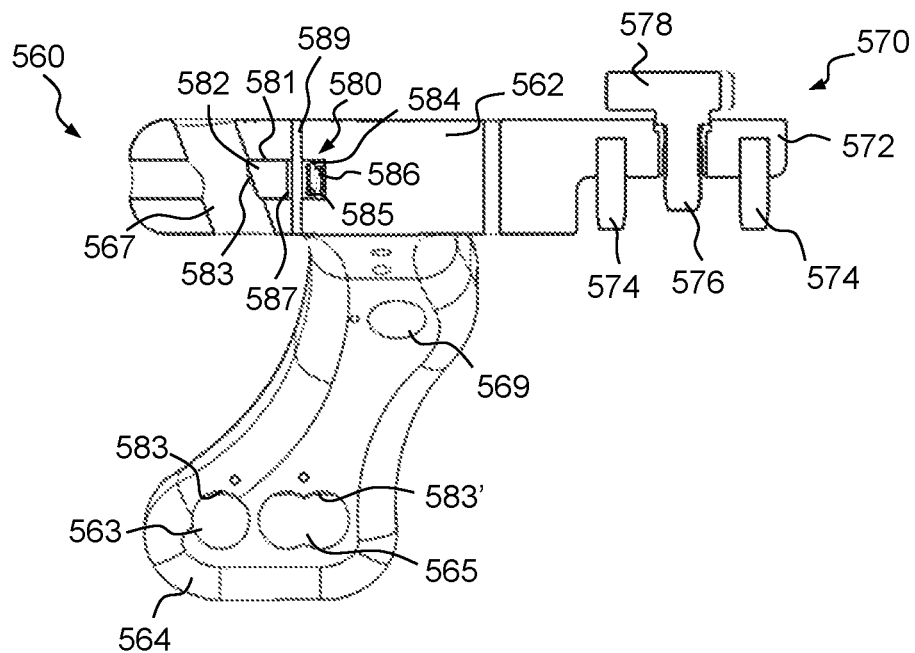
Figure 10:
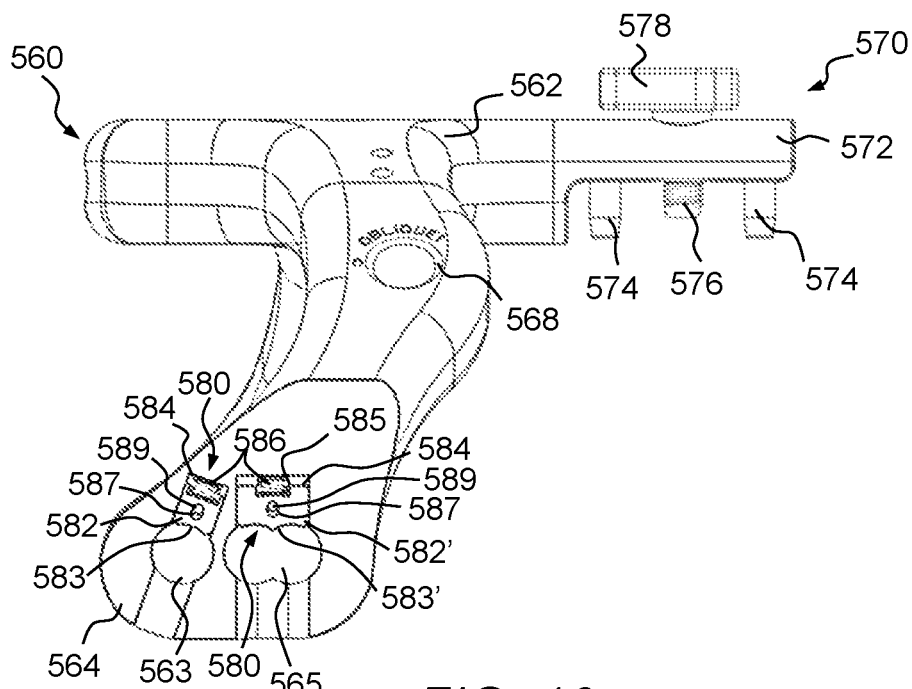
Figure 11:
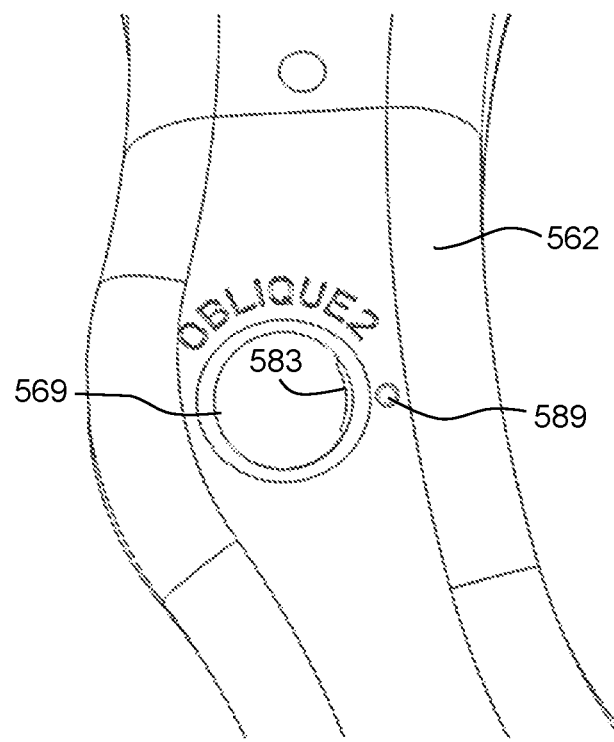

The system 530 includes an insertion tool 540 and an aiming guide 560. Referring to FIGS. 5-7, the insertion tool 540 includes a coupling portion 545 and a handle portion 547. In some embodiments, the coupling portion 545 and the handle portion 547 can be separate parts that are removably joined together, while in other embodiments the coupling portion 545 and the handle portion 547 can be different regions of a single, integrally formed component. The handle portion 547 is preferably rigid, for example, made from stainless steel and carbon fiber and also has provisions to attach an impaction shaft 546 and compression bolt 544. The coupling portion 545 has a connection portion 548 configured to releasably engage or couple to the proximal portion 501 of the nail 500. In the illustrated embodiment, the connection portion 548 includes a pair of projections 549 configured to engage the connection slots 520 on the proximal end 501 of the nail 500, for example with a friction fit. However, those skilled in the art will understand that other coupling mechanisms, for example, a threaded coupling, may be employed.

The handle portion 547 includes a connection assembly 550 for releasably attaching the handle portion 547 to the aiming guide 560. The connection assembly 550 includes a recessed area 552 with a support surface 554 extending between a distal stop surface 551 and a proximal stop surface 553. A pair of non-threaded bores 555 and a threaded bore 556 extend into the support surface 554. The non-threaded bores 555 are configured to receive connection posts 572 of the aiming guide 560 while the threaded bore 556 is configured to receive a screw 574 of the aiming guide 560, as will be described in more detail hereinafter. Those skilled in the art will understand that other connection mechanisms may be employed.

The tibial nail aiming guide 560 is used to install locking screws into the tibial nail 500. The aiming guide 560 sets the trajectory of the locking screws to interface with the proximal openings 515-518 of the nail 500. In at least one embodiment, the aiming guide 560 is made from a radiolucent material. The aiming guide 560 includes an arcuate body 562 which extends between opposed end supports 564. Each end support 564 defines a hole opening 563, which aligns with the ML opening 518, and a slot opening 565, which aligns with the ML slot 517. A plurality of intermediate hole openings 567, 568, 569 are defined along the arcuate body 562, aligned with various openings of the nail 500. More specifically, the hole opening 567 is aligned with the AP oblique opening 516, while the hole openings 568, 569 are each aligned with a respective oblique opening 515.

The openings 563, 565, 567, 568 and 569 are configured to support respective guide sheaths 579. The sheaths 579 are used to protect the soft tissue during the drilling process. The sheaths 579 accept drill sleeves and trocars of various sizes. In the present embodiment, the guide sheaths 579 do not include retention members, but instead, a friction retention assembly 580 is provided in each opening 563, 565, 567, 568, 569. An illustrative friction retention assembly 580 will be described with reference to FIGS. 9-11.

Each friction retention assembly 580 includes a friction pad 582, 582' positioned within a blind bore 581 adjacent to and opening into a respective opening 563, 565, 567, 568, 569. Each friction pad 582, 582' extends from a contact surface 583, 583' to a rear surface 584. The contact surface 583 for the friction pads 582 associated with the openings 563, 567, 568, 569 has an arcuate configuration which complements the outside surface configuration of the sheath 579. The contact surface 583' for the friction pads 582' associated with the openings 565 has two arcuate portions with each complementing the outside surface configuration of the sheath 579 to accommodate the different positions with which the sheath 579 may be aligned with the ML slot 517. Additionally, each contact surface 583, 583' is angled such that it is substantially parallel to the central axis of the respective opening 563, 565 567, 568, 569 (see FIG. 9).

A spring 586 or other biasing member is positioned between the rear surface 584 of the friction pad 582, 582' and the blind end of the bore 581 to bias the friction pad 582, 582' toward the respective opening 563, 565, 567, 568, 569 such that the contact surface 583, 583' extends into the opening 563, 565, 567, 568, 569 such that it may contact and retain the sheath 579. The rear surface 584 of the friction pad 582, 582' may include a notch 585 or the like to retain alignment of the spring 586. To retain the friction pad 582, 582', and thereby the spring 586, within the bore 581, a retaining pin 589 extends through the body 562 and through a slot 587 defined through the friction pad 582, 582'. The slot 587 has a length larger than the diameter of the retaining pin 589 such that the friction pad 582, 582' is axially moveable within the bore 581, with the slot 587 defining the range of motion of the friction pad 582, 582'. The friction pads 582, 582' are generally biased toward the contacting position, however, application of a sufficient force on the sheath 579 will cause the friction pad 582, 582' to move against the force of the spring 586 into the bore 581 whereby the sheath 579 may be advanced or withdrawn.

The aiming guide 560 also includes a connection assembly 570 configured to mate with the connection assembly 550 on the insertion handle 540. The connection assembly 570 includes a body 572 configured to be received within the recessed area 552 of the handle connection assembly 550 with a distal surface 571 contacting the distal stop 551 and a proximal surface 573 contacting the proximal stop surface 553. A pair of connection posts 574 extend from the body 572 and are configured to be received in the non-threaded bores 555 of the connection assembly 550. A rotatable screw 576 with a head 578 extends through the body 572 and is configured to threadably engage the threaded bore 556 to secure the aiming guide 560 with the insertion handle 540. The connector assembly body 575 is a rigid structure and may be made from, for example, metal.

Accordingly, the system 530 provides an insertion handle 547 with reliable and convenient connection assembly for attaching the aiming guide 560. A threaded connection with an accessible head allows tool free connection and disconnection of the aiming guide 560. The insertion handle 547 also contain an external compression bolt 544 used to apply pressure the locking screw in the dynamic position to compress a fracture gap. The aiming guide 560 utilizes friction retention assemblies 580 that lock the soft tissue sheaths 579 in place. The friction retention assembly 580 allows insertion of the soft tissue sheath 579 but prevents it from backing out. This feature helps to maintain the position of the soft tissue sheaths 579 for accurate screw length measurements and facilitates drilling and screw insertion. The aiming guide 560 is designed with extended sheath guides 579 for improved aiming accuracy.

Figure 12:
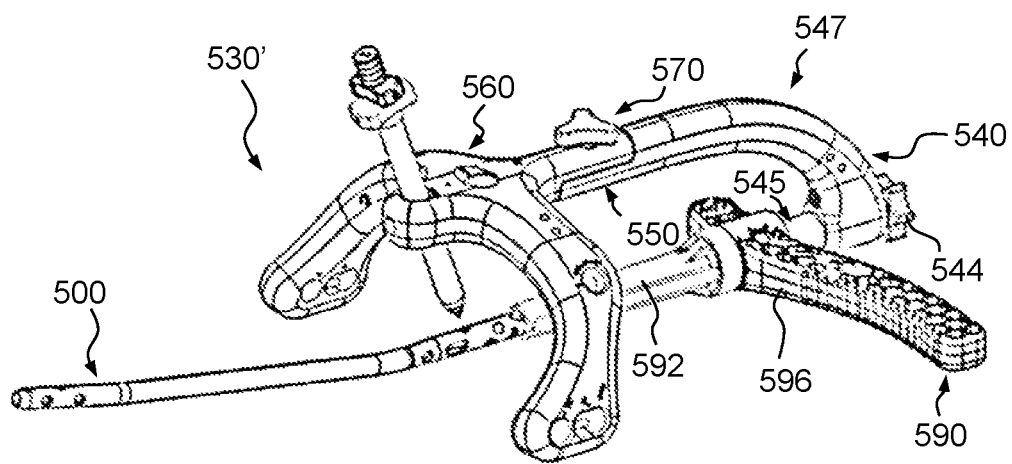

The supra-patellar approach uses a tibia entry point above the knee. A system 530' for use with the supra-patellar approach will be described with reference to FIGS. 12-30. The system 530' is substantially as in the previous embodiment but further includes a cannula assembly 590. As illustrated in FIG. 12, at the time of insertion of the nail 500, the nail 500 and the connection portion 545 of the insertion tool 540 are inserted through the cannula assembly 590. The cannula assembly 590 protects the articular surface of the knee during the nail insertion process. As will be described below, the cannula assembly 590 also protects the articular surface of the knee during reaming. The reaming is performed through a drill guide 610 in the cannula 592 of the cannula assembly 590. Thereafter, the drill guide 610 is removed and nail 500 insertion is performed through the cannula 592 into the entry incision.

Figure 13:
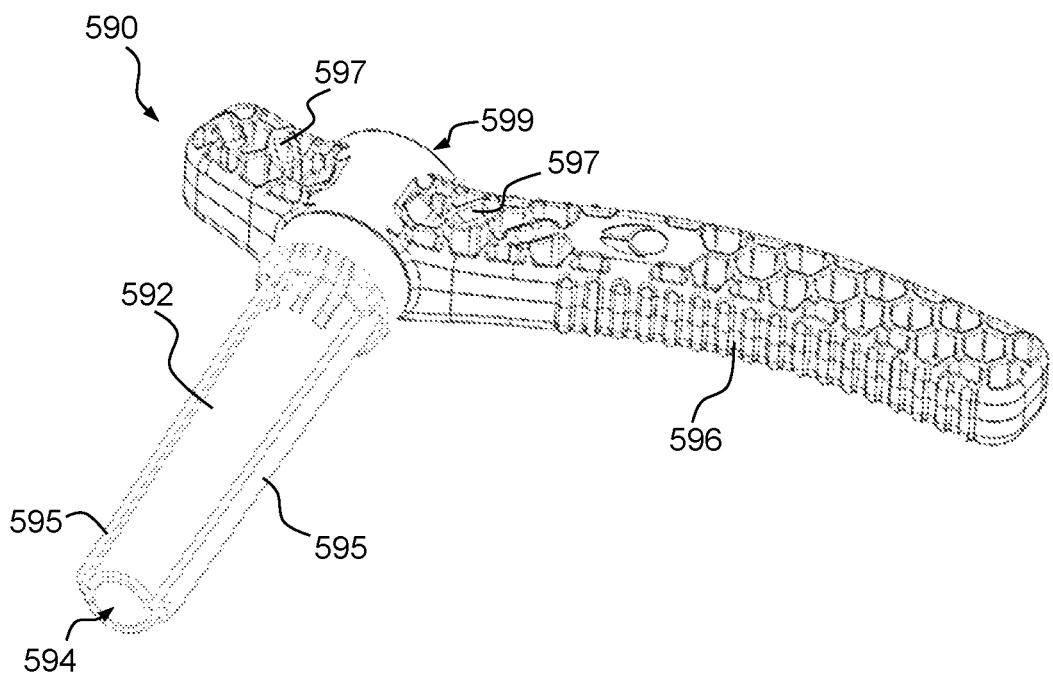
Figure 14:
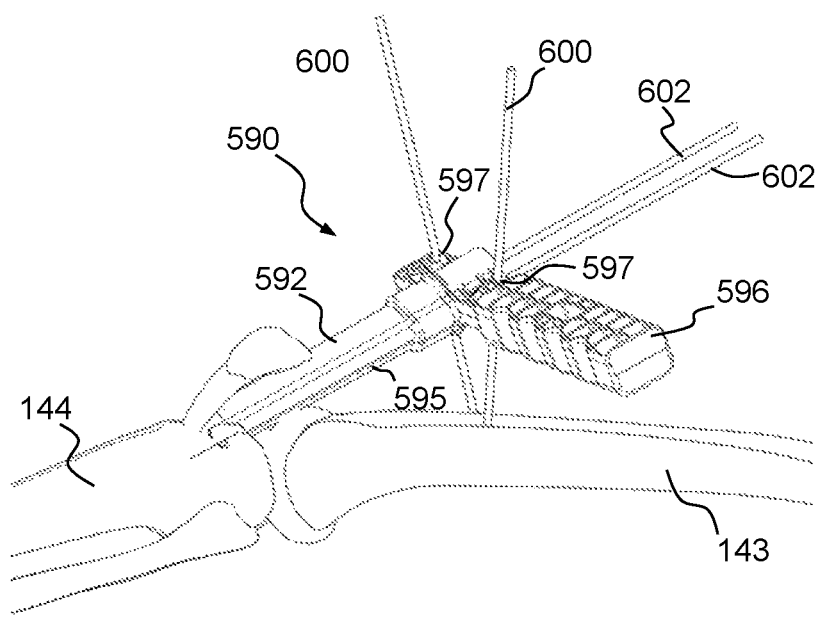

Referring to FIG. 13, an illustrative cannula assembly 590 will be described. The cannula assembly 590 includes a flexible cannula 592 and a rigid handle 596. The cannula 592 has a through passage 594 which is aligned with an opening 599 in the handle 596 to define a continuous passage. The soft, flexible cannula 592 is anatomically shaped to fit between the femoral condyles and minimize damage to the articular surface. In one embodiment, the flexible cannula 592 material is over-molded onto the rigid plastic handle 596. A pair of tibia guide slots 595 extend through the handle 596 and along the sides of the cannula 592. Transverse femur guide holes 597 extend through the handle 596. As shown in FIG. 14, the guide slots 595 and guide holes 597 guide fixation pins 600, 602 into the tibia 144 or femur 143.

The cannula assembly 590 is inserted through an incision in the skin and is the working portal through which the surgeon can perform reaming, drilling, and nail insertion. The guide slots 595 and holes 597 allow the surgeon to fix the cannula 592 in place during the procedure. The guide slots 595 and holes 597 allow the cannula to be fixed to the femur 143 or tibia 144 with converging pins 602, 600 depending on surgeon preference. The cannula 592 is reversible and can be used on either side of the patient.

Figure 15:
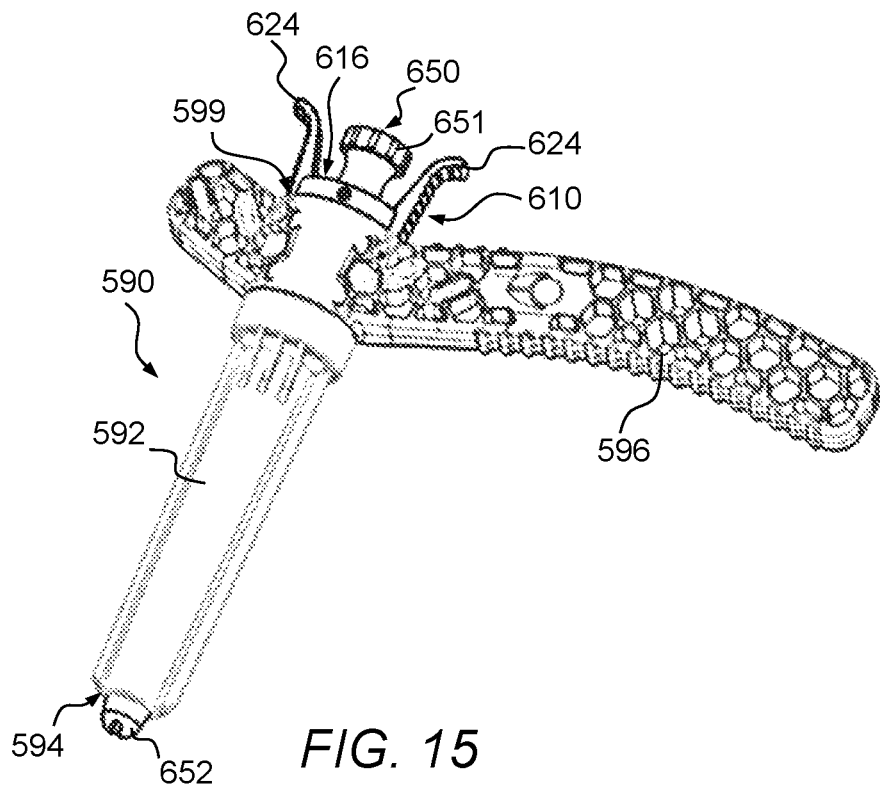
Figure 16:
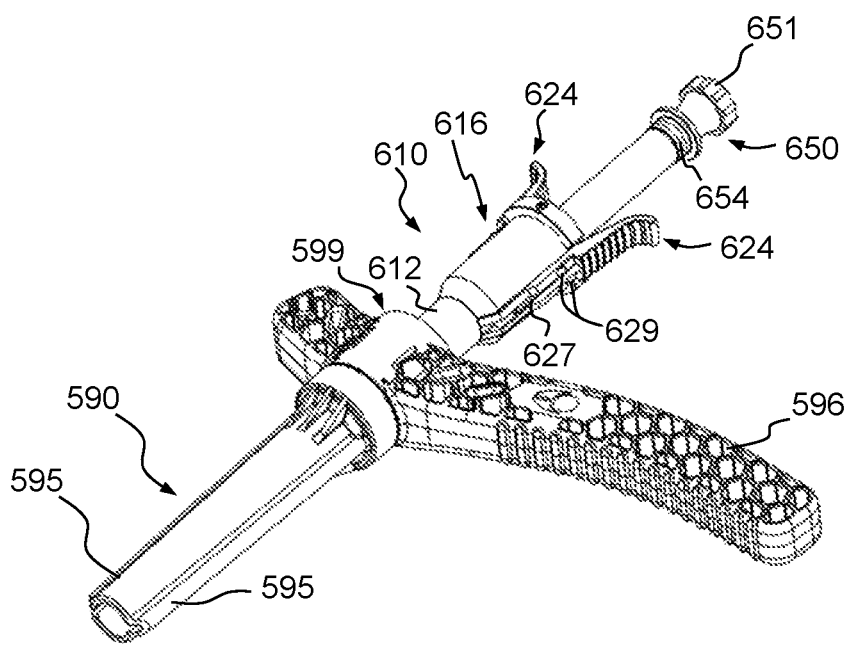
Figures 17, 18:
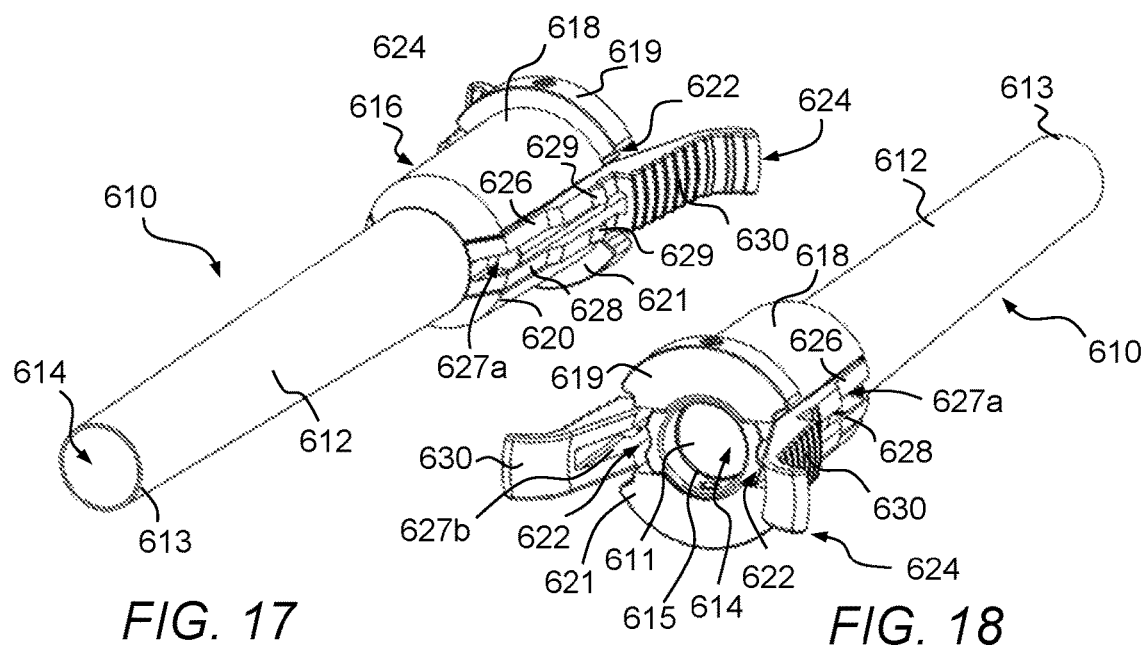
Figures 19, 20:
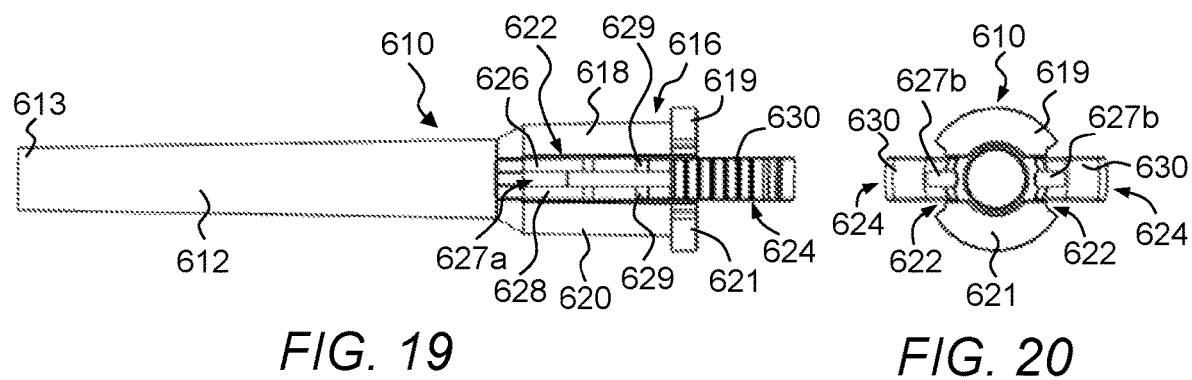

Referring to FIGS. 15-16, the cannula assembly 590 is designed to accept a drill sleeve 610 and round trocar 650. In the illustrated embodiment, the cannula 592 is tapered for easy removal of the drill sleeve 610. The drill sleeve 610 has a sleeve portion 612 configured to slide within the cannula 592 and a housing portion 616 configured to be at least partially received within the opening 599 of the handle 596. In the illustrated embodiment, a pair of release triggers 624 are flexibly supported relative to the housing portion 616 and define projections 629 which engage within the handle 596 to lock the drill sleeve 610 relative to the cannula assembly 590. The release triggers 624 may be flexed toward one another to disengage the projections 629 and remove the drill sleeve 610. As will be described in greater detail hereinafter, each release trigger 624 defines an axial pin slot area 627 which aligns with a respective guide slot 595 of the cannula assembly 590 to facilitate passage of a respective pin 602 through the drill sleeve 610 and cannula assembly 590. The trocar 650 extends from a proximal end 651 to a distal end 652 which is configured to extend from the distal end 613 of the drill sleeve 610. In the illustrated embodiment, a proximal portion of the trocar 650 includes external threads 654 configured to threadably engage internal threads 615 of the drill sleeve 610 (see FIG. 18).

Turning to FIGS. 17-22, the drill sleeve 610 will be described in more detail. The drill sleeve 610 includes the sleeve portion 612 extending from a proximal end 611 to a distal end 613 with a passage 614 extending therethrough. The housing portion 616 is secured about the proximal end 611 of the sleeve portion 612. The housing portion 616 of the present embodiment includes two housing halves 618, 620 which each extend less than 180° such that an axial gap 622 is defined between the halves 618, 620 on each side of the housing portion 616. Each of the housing halves 618, 620 defines a respective radial flange 619, 621 which together define a stop which contacts the cannula handle 596.

Figures 21, 22:
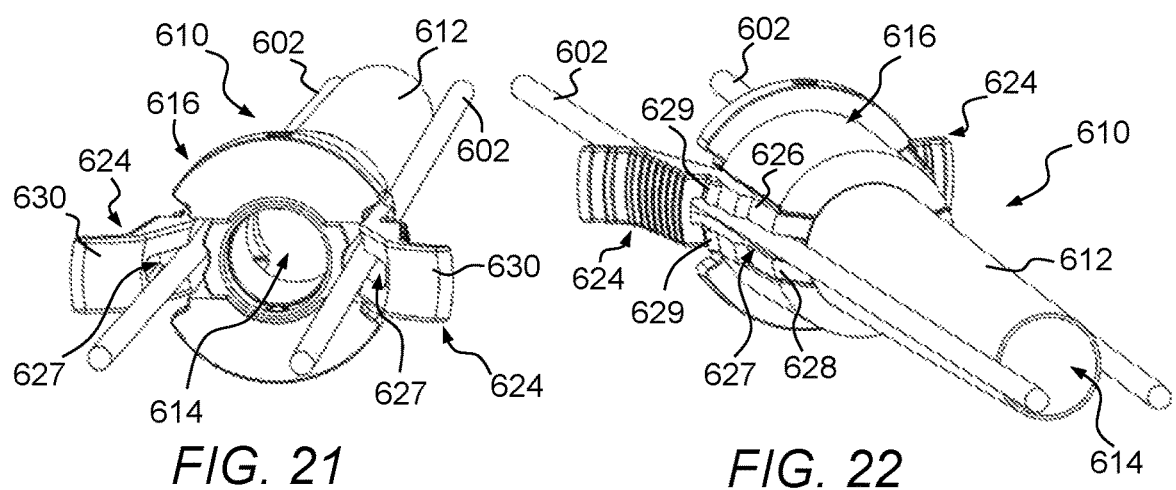
Figure 23:
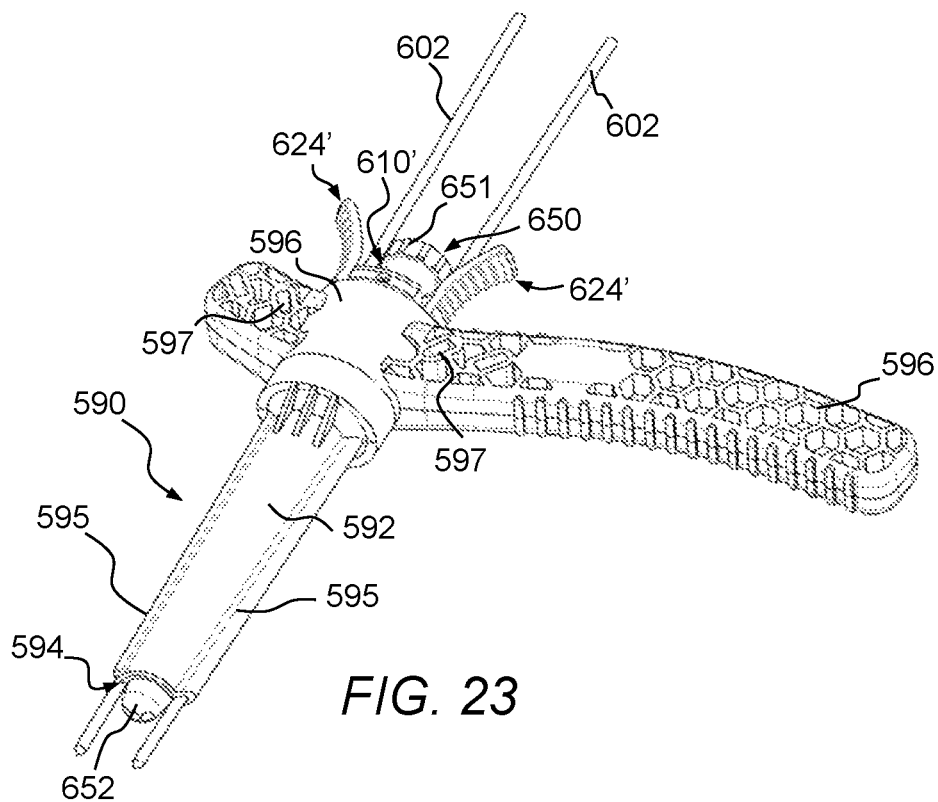
Figure 24:
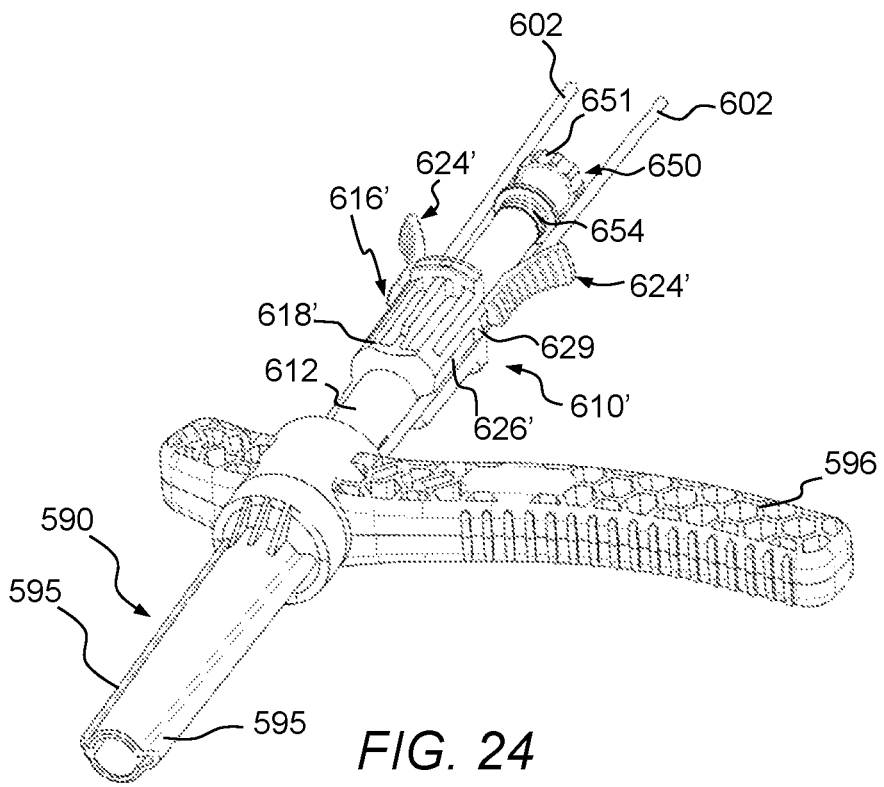

A release trigger 624 is positioned within each axial gap 622. Each trigger 624 is defined by a pair of spaced apart arms 626, 628 which are each hingedly connected at one end to the housing portion 616 and at the other end are interconnected to one another by a trigger handle 630. A projection 629 extends outward from each of the arms 626, 628. The space 627*a* between the arms 626, 628 defines a first portion of the axial pin slot area 627 while a notch 627*b* on the radial inner surface of the trigger handle 630 defines the remainder of the axial pin slot area 627. The axial pin slot areas 627 allow passage of the pins 602 externally past the housing portion 616 and the sleeve portion 612 as shown in FIGS. 21 and 22. The illustrated trigger handles 630 have a curved configuration with ridges to facilitate gripping of the release triggers 624, however, it is understood that they may have different configurations.

Referring to FIGS. 23-30, an alternative drill sleeve 610' will be described. Again, the cannula assembly 590 is designed to accept the drill sleeve 610' and round trocar 650. The drill sleeve 610' has a sleeve portion 612 configured to slide within the cannula 592 and a housing portion 616' configured to be at least partially received within the opening 599 of the handle 596. In the illustrated embodiment, a pair of release triggers 624' are flexibly supported relative to the housing portion 616' and define projections 629 which engage within the handle 596 to lock the drill sleeve 610' relative to the cannula assembly 590. The release triggers 624' may be flexed toward one another to disengage the projections 629 and remove the drill sleeve 610'. As will be described in greater detail hereinafter, each release trigger 624' defines an axial shelf 631 which aligns with a respective guide slot 595 of the cannula assembly 590 to facilitate passage of a respective pin 602 past the drill sleeve 610 and through the cannula assembly 590.

Turning to FIGS. 25-30, the drill sleeve 610' will be described in more detail. The drill sleeve 610' includes the sleeve portion 612' extending from a proximal end 611 to a distal end 613 with a passage 614 extending therethrough. The housing portion 616' is secured about the proximal end 611 of the sleeve portion 612. The housing portion 616' of the present embodiment includes two housing halves 618', 620'. Each of the housing halves 618', 620' defines a respective radial flange 619', 621' which together define a stop which contacts the cannula handle 596. In the present embodiment, the housing half 620' extends between side wall surfaces 625 which will define a first surface portion of a guide area 632 for guiding the posts 602. The release triggers 624' extend from the other housing half 618', above a central plane of the drill sleeve 610', and define contact surfaces 631 which define a second surface portion of the guide area 632.

Figure 29:
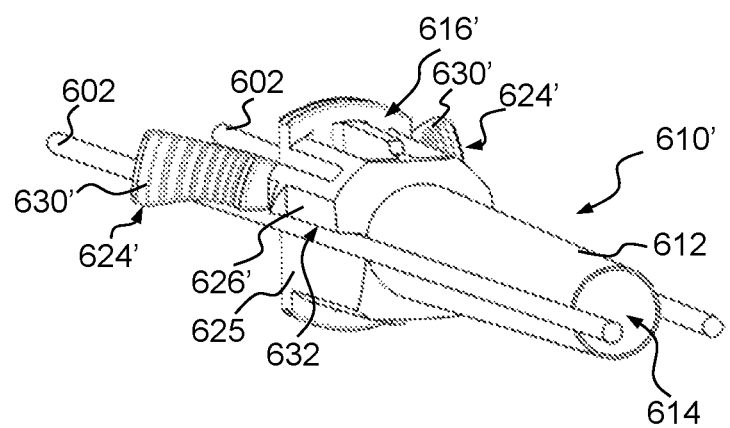
Figure 30:
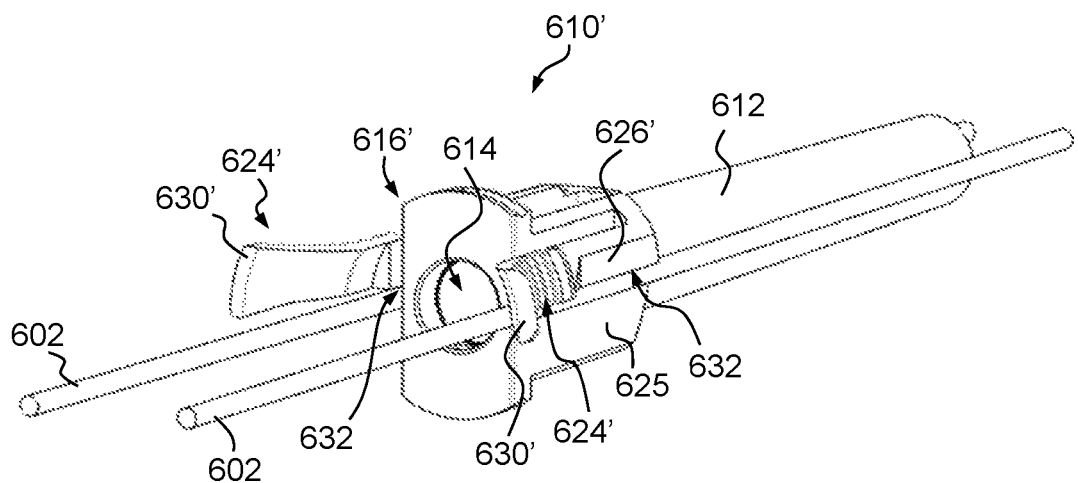

Each trigger 624' of the present embodiment is defined by a single arm 626' which is hingedly connected at one end to the housing half 618' and at the other end is connected to the trigger handle 630'. A projection 629 extends outward from each of the arms 626. As described above, each of the release triggers 624' extends above a central plane of the drill sleeve 610' such that a lower surface 631 of the arm 626' is also above the central plane of the drill sleeve 610'. The lower surface 631 is generally perpendicular to a respective side wall surface 625 such that the surfaces 625, 631 define a guide area 632 aligned with a respective guide slot 595 of the cannula assembly 590. The guide areas 632 allow passage of the pins 602 externally past the housing portion 616' and the sleeve portion 612 as shown in FIGS. 29 and 30. The illustrated trigger handles 630' have a curved configuration with ridges to facilitate gripping of the release triggers 624', however, it is understood that they may have different configurations.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

From the foregoing, it will be appreciated that specific embodiments of the invention have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. An insertion tool for inserting an intramedullary nail into a bone, the insertion tool comprising:

an aiming guide having an arcuate body defining at least two hole openings therethrough, each of the hole openings axially aligned with a respective opening in the intramedullary nail and configured to receive a guide sheath therethrough, wherein a friction retention assembly is associated with each hole opening and includes a friction pad which retractably extends into the hole opening to engage a guide sheath positioned therein, and wherein a pin extends through a portion of the arcuate body and through a slot defined through the friction pad, the slot having a length greater than a diameter of the pin such that the friction pad is moveable over a range of motion defined by the slot.

2. The insertion tool of claim 1, wherein the friction pad is positioned in a blind bore adjacent to and opening into the hole opening.

3. The insertion tool of claim 2, wherein a biasing member is positioned between the friction pad and a closed end of the blind bore to bias the friction pad toward the hole opening.

4. The insertion tool of claim 1, wherein each friction pad has a contact surface having a configuration which complements an outer surface of a guide sheath positioned in the respective hole opening.

5. The insertion tool of claim 1, wherein each friction pad has a contact surface which extends in a plane which is substantially parallel to a central axis of the respective hole opening.

6. A drill sleeve for inserting an intramedullary nail into a bone, the drill sleeve comprising:

a sleeve portion configured to be received in a flexible cannula of a cannula assembly, wherein the flexible cannula extends from a rigid handle;

a housing portion from which the sleeve portion extends, the housing portion configured such that a portion thereof is received in a through passage extending through the rigid handle; and a pair of release triggers hingedly connected to the housing portion, each release trigger defining at least one projection configured to releasably engage within the rigid handle to lock the drill sleeve relative to the cannula assembly, wherein each of the release triggers defines a guide area which is configured to align with an axial pin slot of the cannula assembly such that a fixation pin may be passed beyond the housing portion and through the axial pin slot, and wherein the axial pin slot of the cannula assembly extends adjacent to the through passage.

7. The drill sleeve of claim 6, wherein each of the triggers includes a pair of spaced apart arms with one end thereof hingedly connected to the housing portion and the opposite ends interconnected by a trigger handle, wherein the space between the arms defines a portion of the guide area.

8. The drill sleeve of claim 7, wherein a respective projection is defined on each of the arms.

9. The drill sleeve of claim 6, wherein each of the triggers includes an arm with one end thereof hingedly connected to the housing portion and the opposite ends connected to a trigger handle, wherein a lower surface of the arm and a side wall surface of the housing portion define the guide area.

10. The drill sleeve of claim 9, wherein a respective projection is defined on each of the arms.

* * * * *